US012697371B2

(12) United States Patent (10) Patent No.: US 12,697,371 B2
Zhou (45) Date of Patent: Aug. 4, 2026

(54) METHOD FOR PREVENTING, TREATING OR DELAYING MYOCARDIAL DAMAGE USING NEUREGULIN AND COMPOSITION

(71) Applicant: ZENSUN (SHANGHAI) SCIENCE & TECHNOLOGY, CO., LTD., Shanghai (CN)

(72) Inventor: Mingdong Zhou, New South Wales (AU)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 958 days.

(21) Appl. No.: 17/420,974

(22) PCT Filed: Jan. 3, 2020

(86) PCT No.: PCT/CN2020/070299
§ 371 (c)(1),
(2) Date: Jul. 6, 2021

(87) PCT Pub. No.: WO2020/143548
PCT Pub. Date: Jul. 16, 2020

(65) Prior Publication Data
US 2022/0096599 A1     Mar. 31, 2022

(30) Foreign Application Priority Data

Jan. 7, 2019     (CN) .......................... 201910015257.7
Dec. 31, 2019     (CN) .......................... 201911412811.1

(51) Int. Cl.
*A61K 38/18*          (2006.01)
(52) U.S. Cl.
CPC ................................. *A61K 38/1883* (2013.01)
(58) Field of Classification Search
CPC ... A61K 38/1883; C07K 14/4756; A61P 9/10; A61P 9/00
See application file for complete search history.

(56) References Cited

U.S. PATENT DOCUMENTS

| | | | | |
|---|---|---|---|---|
| 8,785,387 B2 * | 7/2014 | Zhou | .......................... | A61P 9/02 514/14.9 |
| 9,089,524 B2 * | 7/2015 | Zhou | ....................... | A61P 29/00 |
| 9,655,949 B2 * | 5/2017 | Zhou | ....................... | A61P 29/00 |
| 10,098,834 B2 * | 10/2018 | Zhou | .................. | A61K 38/1883 |
| 10,894,815 B2 * | 1/2021 | Zhou | .......................... | A61P 3/10 |
| 11,179,323 B2 * | 11/2021 | Zhou | .......................... | A61P 9/04 |
| 11,246,909 B2 * | 2/2022 | Zhou | .................. | G06V 40/1306 |
| 11,253,573 B2 * | 2/2022 | Zhou | ....................... | A61K 45/06 |
| 11,638,746 B2 * | 5/2023 | Zhou | ....................... | A61K 48/00 514/8.3 |
| 11,826,400 B2 * | 11/2023 | Zhou | ....................... | A61K 45/06 |
| 12,076,370 B2 * | 9/2024 | Zhou | ....................... | A61K 45/06 |

FOREIGN PATENT DOCUMENTS

| | | | | |
|---|---|---|---|---|
| CN | 1498656 | A | * | 5/2004 |
| CN | 101491670 | A | | 7/2007 |
| CN | 102139095 | A | | 8/2011 |
| CN | 102245189 | A | | 11/2011 |
| CN | 103768582 | A | | 5/2014 |
| CN | 110167564 | A | | 8/2019 |
| JP | 2017125032 | A | | 7/2017 |
| WO | WO 2010/142141 | A1 | | 12/2010 |
| WO | WO 2014/138502 | A1 | | 9/2014 |
| WO | WO 2014/187342 | A1 | | 11/2014 |
| WO | WO 2016/058493 | A1 | | 4/2016 |
| WO | 2017053794 | A1 | | 3/2017 |

OTHER PUBLICATIONS

International Search Report issued on PCT/CN2020/070299, dated Mar. 12, 2020.
Zensun USA Inc., 2013, "Zensun Announces Positive Clinical Results for Neucardin(TM) to Improve Heart Function and Reduce Mortality in Chronic Heart Failure Patients," PR Newswire (5 pages) Available online at: https://www.prnewswire.com/news-releases/zensun-announces-positive-clinical-results-for-neucardintm-to-improve-heart-function-and-reduce-mortality-in-chronic-heart-failure-patients-208632041.html.
Xu et al., 2010, "Neuregulin-1/ErbB Signaling and Chronic Heart Failure," Advances in Pharmacology 59:31-51.

* cited by examiner

*Primary Examiner* — Sudhakar Katakam
(74) *Attorney, Agent, or Firm* — Jones Day

(57) ABSTRACT

A method for preventing, treating or delaying myocardial damage in a mammal using neuregulin and a composition. An administration method for, an administration frequency of and an administration dosage of a pharmaceutical formulation or composition for reducing myocardial damage. It can be proved in a rat myocardial damage model that neuregulin can improve the cardiac function after myocardial infarction, suggesting that neuregulin can be used for preventing, treating, or delaying myocardial infarction damage.

8 Claims, 4 Drawing Sheets
Specification includes a Sequence Listing.

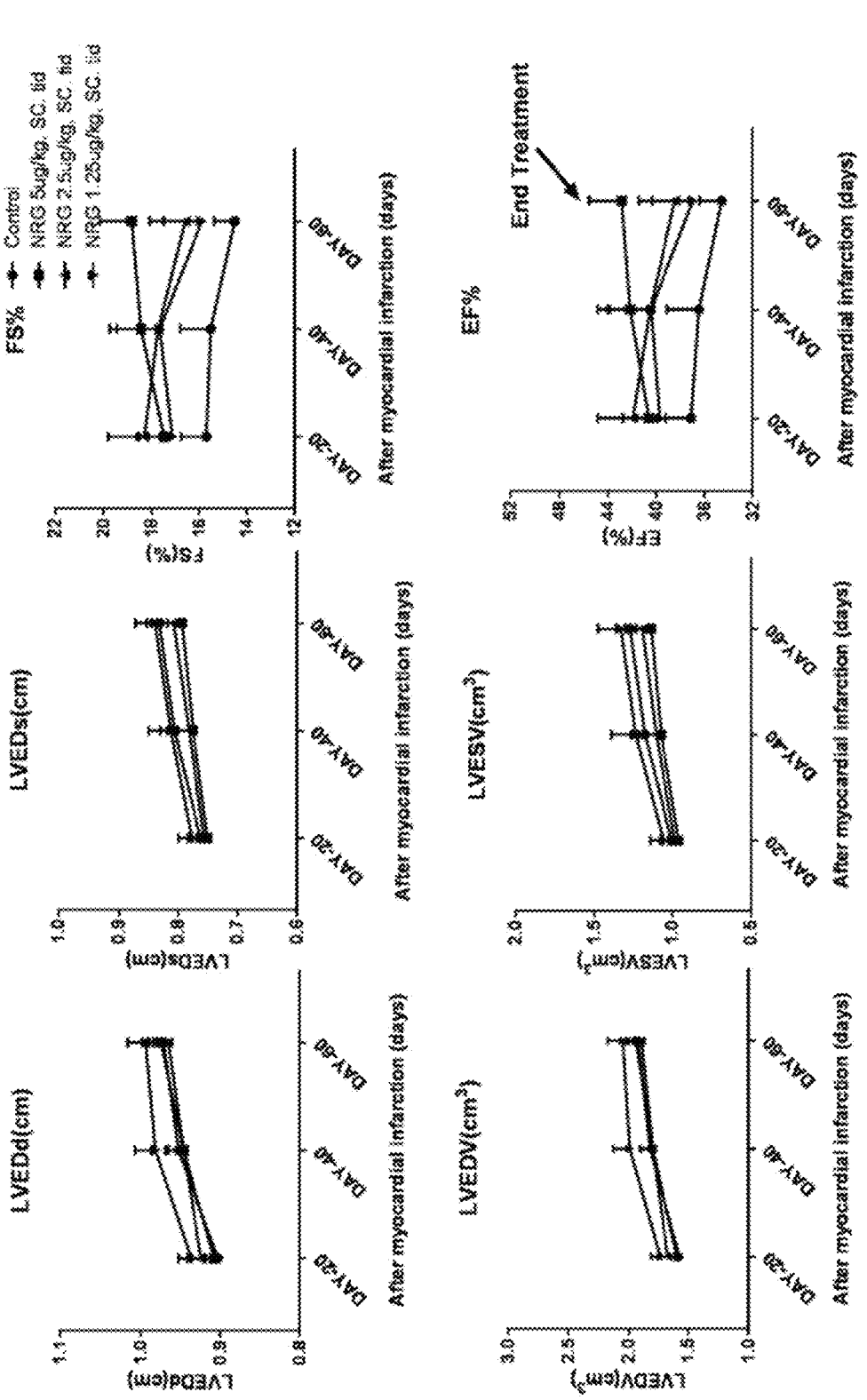
Figure 1: Echocardiographic results of the effect of NRG in treating rats with acute myocardial infarction through long-term subcutaneous administration of different doses.

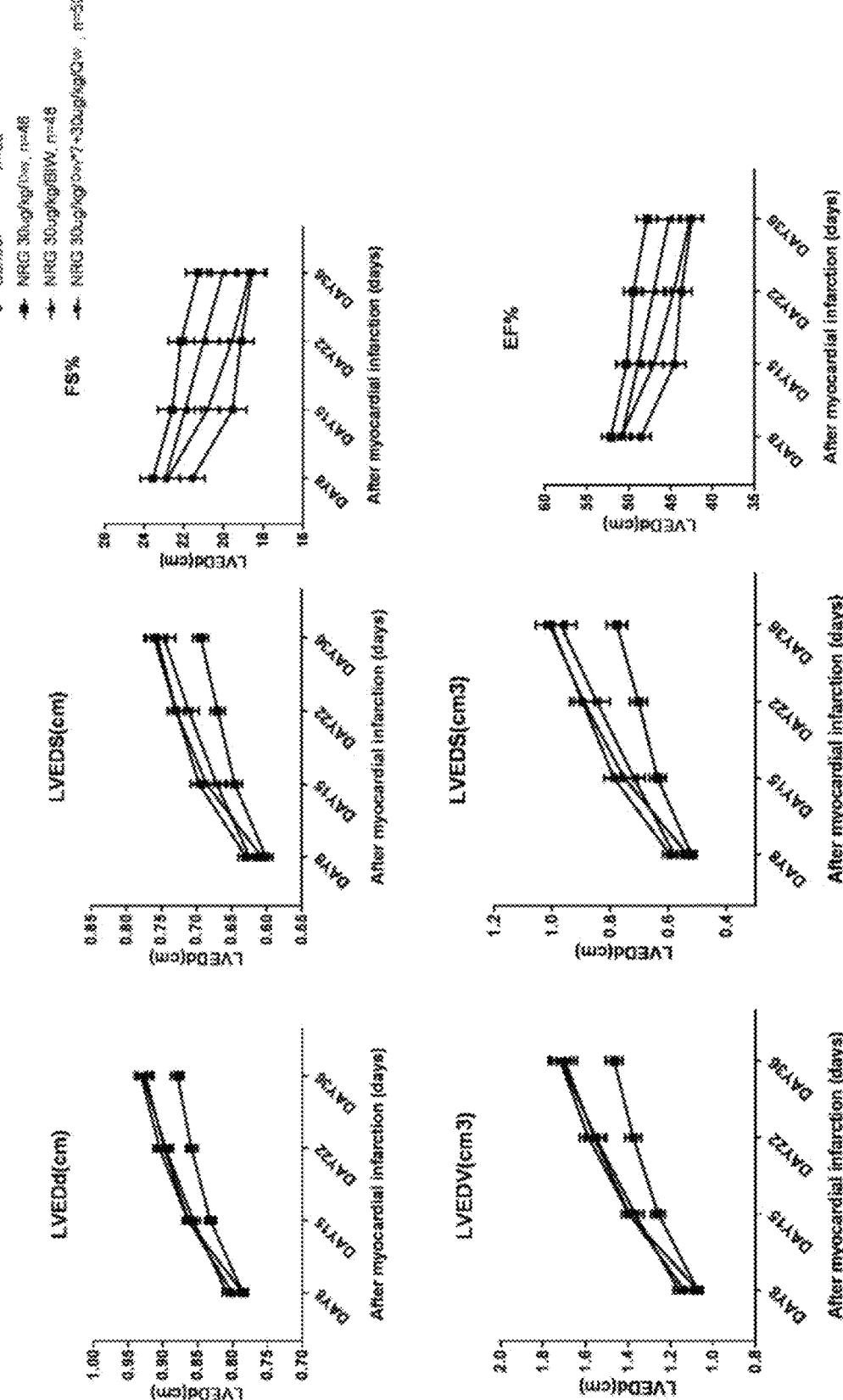
Figure 2: Echocardiographic results of the effect of NRG in treating rats with acute myocardial infarction through long-term subcutaneous administration at different frequencies.

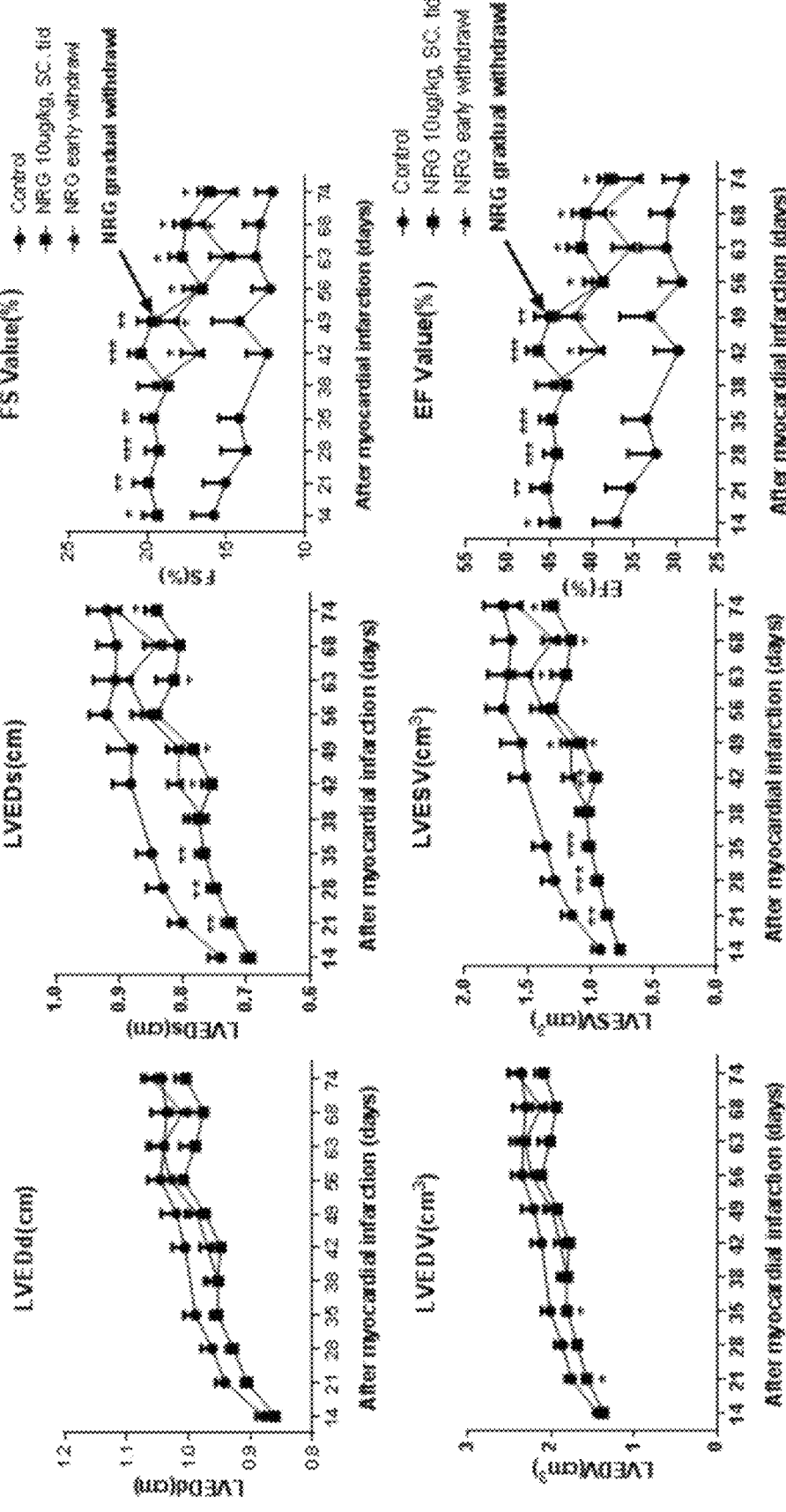
Figure 3: Therapeutic effect of NRG on acute myocardial infarction in rats through long-term subcutaneous administration followed by withdrawal through frequency reduction.

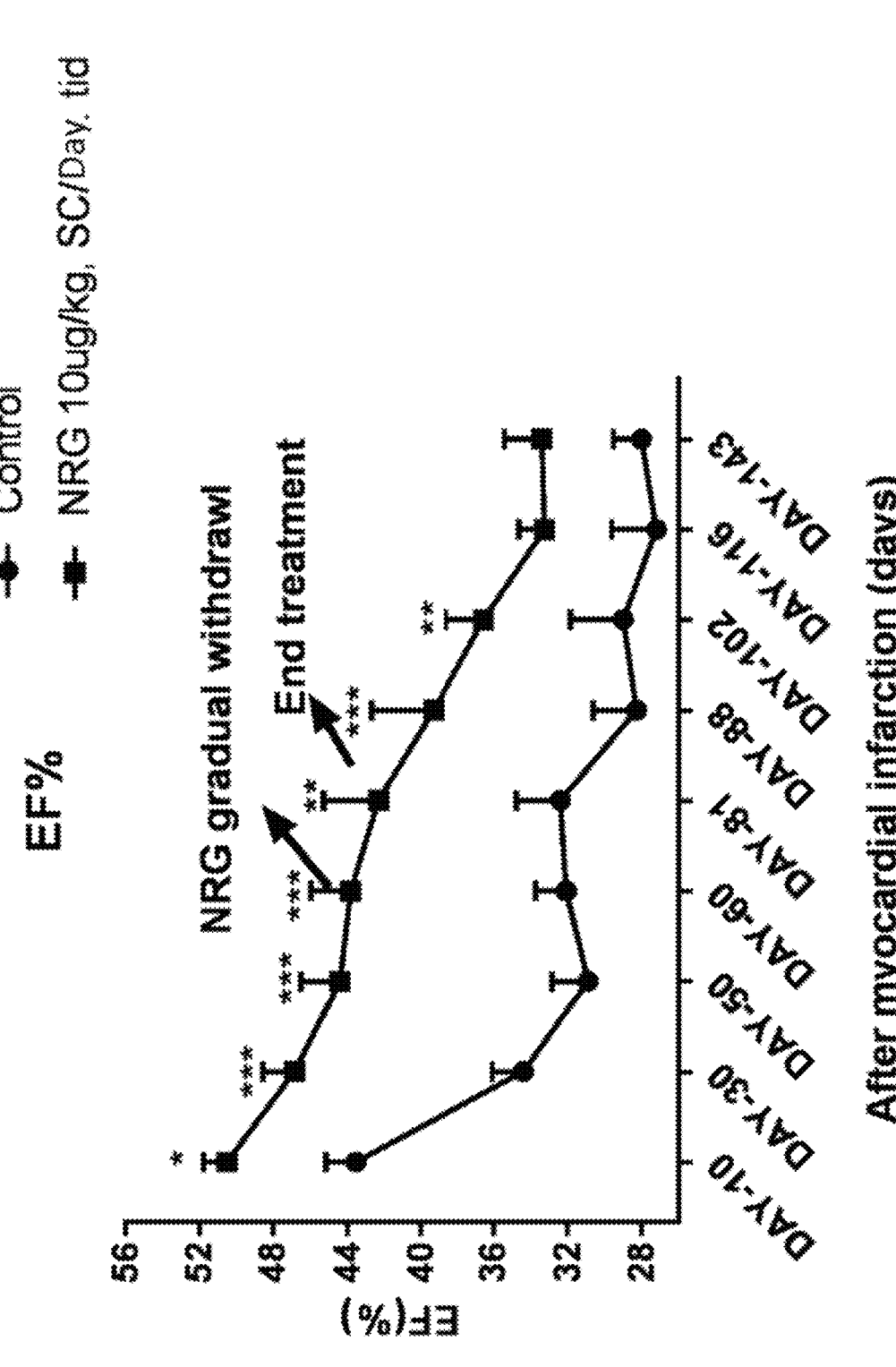
Figure 4: Therapeutic effect of NRG on acute myocardial infarction in rats through long-term subcutaneous administration followed by withdrawal through dose reduction

METHOD FOR PREVENTING, TREATING OR DELAYING MYOCARDIAL DAMAGE USING NEUREGULIN AND COMPOSITION

CROSS-REFERENCE TO RELATED APPLICATIONS

This application is a U.S. National Stage Application under 35 U.S.C. § 371 of International Patent Application No. PCT/CN2020/070299, filed Jan. 3, 2020, which claims priority to Chinese Patent Application No. 201911412811.1, filed Dec. 31, 2019, and Chinese Patent Application No. 201910015257.7, filed Jan. 7, 2019, the disclosure of each of which is incorporated by reference herein in its entirety.

SEQUENCE LISTING

This application incorporates by reference in its entirety the Computer Readable Form of a Sequence Listing in ASCII text format submitted via EFS-Web. The Sequence Listing text file submitted via EFS-Web is entitled "11748-098-999_SEQ_LISTING.txt," was created on Jul. 6, 2021 and is 1,037 bytes in size.

FIELD OF THE INVENTION

The present invention relates to the use of neuregulin (NRG) for the preparation of a drug for preventing, treating or relieving myocardial injury in mammals. The present invention also relates to a method of administration, a frequency of administration and an administered dose of the pharmaceutical preparation or composition containing NRG for preventing, treating or relieving myocardial injury in mammals. In particular, the present invention relates to a method for preventing, treating or relieving myocardial injury and a pharmaceutical composition containing NRG therefor, and a method of administration, a frequency of administration and an administered dose of the pharmaceutical preparation or composition containing NRG for preventing, treating or relieving myocardial injury in mammals.

BACKGROUND OF THE INVENTION

Cardiovascular problems pose a serious threat to the people's lives and health on a global scale. There are many types of cardiovascular diseases, including heart failure, myocardial infarction, coronary atherosclerotic heart disease, arrhythmia, cardiomyopathy, valvular heart disease, infective endocarditis, pericardial disease, ischemic heart disease, congenital heart disease, etc. A cardiovascular disease tends to cause myocardial injury and affect the cardiac function, thereby making the human body unhealthy. Myocardial infarction is a cardiovascular disease that seriously endangers the human health. As the people's living conditions are continuously ameliorated, the incidence of ischemic myocardial infarction increases steadily. Myocardial infarction is a type of ischemic myocardial necrosis that is mostly induced by severe and chronic myocardial ischemia caused by sharp reduction or interruption in coronary blood supply due to persistent blockade in the coronary artery. Ischemic myocardial infarction causes cardiomyocyte necrosis and scarring, thereby affecting the cardiac function.

When myocardial infarction occurs, the coronary artery is occluded for 20-30 min, leading to necrosis of some cardiomyocytes owing to blood insufficiency, starting the pathological process of myocardial infarction. As myocardial necrosis becomes severer and severer, most of the affected cardiomyocytes gradually suffer from coagulative necrosis 2 hours later, while the myocardial interstitium is congestive and oedematous, accompanied by abundant inflammatory cell infiltration. The myocardial necrosis process almost comes to an end 6-12 hours later. The myocardial fibers dissolve 1-2 weeks later, i.e., it is swallowed by macrophages, getting gradually fibrillated until the necrotic zone is completely replaced by dense fibrous scars 6 weeks later. This is known as old or healed myocardial infarction.

The normal function of the left ventricle is significantly affected after the occurrence of myocardial infarction. If the heart suffers from ischemia on a large scale, the pumping function of the left ventricle may be impaired, leading to a decrease in cardiac output, stroke volume and blood pressure while an increase in end-systolic volume and a rise in end-diastolic volume within several weeks after the infarction.

Ventricular remodeling is an important pathological behavior that occurs following myocardial infarction. Post-infarction ventricular remodeling refers to a change that takes place in the structure and morphology of the ventricular infarct area and non-infarct area after the occurrence of myocardial infarction: The change in the infarct area mainly includes infarct expansion while the change in the non-infarct area is primarily manifested in ventricular enlargement. The typical manifestation of ventricular remodeling is ventricular decompensated hypertrophy; a change in the ventricular mass, volume gain and morphologic alteration can cause ventricular pumping dysfunction, which may progress into heart failure. The basic mechanism that causes the occurrence and progression of heart failure is ventricular remodeling. The symptom is a persistent and progressive change second to myocardial infarction. Its severity determines the patient's cardiac function and prognosis. Post-infarction ventricular remodeling is one of the major cardiovascular diseases that affects the patient's cardiac function and endangers the human life.

Currently, the major therapies for myocardial infarction include early-stage reperfusion (including thrombolytic therapy and interventional therapy), angiotensin (ANG) II receptor blocker, angiotensin converse enzyme (ACE) inhibitor, β-receptor blocker, etc., which are effective in reducing the infarct size, reducing recurrent myocardial ischemia, improving revascularization and suppressing excessive ventricular dilatation, thereby decreasing the incidence of chronic heart failure.

The symptoms of myocardial infarction are closely related to the infarct size and site and the conditions of coronary collateral vessels. The cardinal symptoms include pain, fever, tachycardia, nausea, vomiting, hypotension, shock, arrhythmia, etc. The main complications of myocardial infarction include papillary muscle dysfunction or rupture, heart rupture, ventricular aneurysm, embolism, post-infarction syndrome (PMIS), etc.

Most of the existing drugs or interventional therapies can only allay the symptoms of myocardial infarction, and cannot repair cardiac tissue injury. For patients with advanced myocardial infarction, although heart transplant, as the last treatment choice, can improve the cardiac function and save dying patients, it can hardly have a widespread application in clinical practice owing to the scarcity of donors, the complexity of surgery, immunological rejection and high treatment costs.

To sum up, the myocardial injury caused by a cardiovascular disease causes a serious harm to human health. Especially, as a fatal disease that seriously endangers human health, myocardial infarction needs to be treated with a safer and more effective drug in clinical practice.

Neuregulin (NG) or heregulin (HRG), which is a member of the EGF-like family, refers to a group of growth differentiation factors (GDFs) structurally similar to one another, including NRG1, NRG2, NRG3 and NRG4, as well as their isomers, which exert a series of biological effects in stimulating breast cancer cell differentiation and lactoprotein secretion (Lessor T et al., J Cell Biochem. 1998; 70 (4): 587-595); inducing the differentiation of neural crest cells into Schwann cells (Topilko et al., Mol Cell Neurosci, 1996; 8 (2-3): 71-75); stimulating the synthesis of acetylcholine receptors in skeletal muscle cells (Altiok N et al., EMBO. J. 1995; 14 (17): 4258-4266); promoting cardiocyte survival and DM synthesis (Zhao Y Y et al. I Biol Cher. 1998; 273 (17): 10261-10269). An in-vivo study conducted in mouse embryos with severe NRG gene deficiency proved the necessity of NRG for cardiac and nerve development.

The NRG receptors are members of the EF receptor family, including FR, ErbB2, ErbB and ErbB4, which play an important role in cell growth, differentiation, survival, etc. They are tyrosine kinase receptors, composed of the extracellular ligand-binding domain, transmembrane domain and intracellular tyrosine kinase domain. When NRG binds to the extracellular domain of ErbB3 or ErbB4, a conformational change takes place in it, thereby causing the formation of ErbB3/ErbB4 or ErbB2/ErbB3 heterodimers or ErbB4/ErbB4 homodimers, and causing the phosphorylation of its C-terminus. The phosphorylated C-terminus can further bind to the downstream signaling proteins in the cells to activate the AKT and/or EK signaling pathways, ultimately causing a series of cell responses such as stimulation or inhibition of cell proliferation, cell differentiation, cell apoptosis, cell migration or cell adhesion. Among these receptors, ErbB2 and ErhB4 are mainly expressed in the cardiac tissues (Zhao Y Y et al., Circ Res. 1999; 84 (12): 1380-1387).

Existing evidence shows that the EGF-like domain of NRG-1, which contains 50-64 amino acid, is highly capable of binding to and activating the receptors (Culousoou J M et al., J Biol Chem. 1995; 270 (21): 12857-12863). NKG-1β can bind to ErbB3 and ErbB4 with high affinity. ErbB2 can form a heterodimer with ErbB3 or ErhB4, and its affinity for the ligand is higher than that of the ErbB3 or ErbB4 homodimer for the ligand. The neurodevelopmental studies confirm that the formation of the sympathetic nervous system requires signal transduction via NRG-1β, ErbB2 and ErhB3 (Britsch S et al., Dienes Dev. 1998; 12 (12): 1825-1836). When the expression of NRG-1β or ErbB2 or ErbB4 is distributed, embryonic death is caused by cardiac developmental defects (Gassmann M et al., Nature, 1995; 378 (6555): 390-394). Recent studies indicate that NRG-1β, ErbB2, and ErbB4 not only are essential for cardiac development, but also play a very important role in maintaining the cardiac function of adults (Kuramochi Y et al., J Mol Cell Cardial. 2006; 41 (2): 228-235). NRG-1β has been proved to be able to strengthen the formation of myocardial sarcomeres in adults. It has been found in various animal models of heart failure that the intake of MRG-1β EGF-like domain can ameliorate the cardiac function to prevent cardiac dysfunction (Liu et al., J Am Coll Cardiol. 2006; 48: 1438-1447). In clinical trials, NRG also showed a therapeutic effect on chronic heart failure caused by various etiological factors, significantly enhancing the cardiac function (CN200910057390.5). In the animal model of cerebral ischemia-reperfusion, NRG-1 also showed a significant protective effect on the brain cells, inhibiting brain cell apoptosis, enhancing the neurologic function and reducing the infarct size (Li Q et al., Neurosci Lett. 2008; 443 (3): 155-159). There is evidence that cardiac ischemia-reperfusion induces the release of NRG-1 and activates the NRG/ErbB signaling pathway in cardiocytes (Kuramochi Y et al., J Biol Chem. 2004; 279 (49): 51141-51147), and that NRG-1 plays a role in preventing, treating or relieving cardiac ischemia-reperfusion injury (WO2011091723).

Myocardial injury is a fatal disease that severely endangers human health, but the method of administration, frequency of administration and administered dose of NRG-1 for the treatment of myocardial injury have yet to be clearly determined. The present invention provides a method and pharmaceutical composition containing NRG therefor to meet the above needs. It is worth mentioning that the present invention particularly provides an optimized frequency of administration, the present invention particularly provides an optimized administered dose, and the present invention particularly provides an optimal method of administration. The present invention further relates to the use of NRG in the preparation of a drug for preventing, treating or relieving myocardial injury in mammals. For the treatment of myocardial infarction, the present invention particularly provides an optimized frequency of administration, the present invention particularly provides an optimized administered dose, and the present invention particularly provides an optimal method of administration.

DETAILED DESCRIPTION

A. Summary

The present invention provides uses of NRG for the preparation of a drug for preventing, treating or relieving myocardial injury in mammals. The present invention further relates to the use of NRG for the preparation of a drug for preventing, treating or relieving myocardial injury in mammals, and the mammals are preferably humans. NRG can improve the cardiac function affected by myocardial injury and reduce cardiac remodeling.

Many cardiovascular diseases, such as heart failure, myocardial infarction, coronary atherosclerotic heart disease, arrhythmia, myocarditis, valvular heart disease, infective endocarditis, pericardial disease, ischemic heart disease, congenital heart disease, etc., can cause myocardial injury. Myocardial injury affects the cardiac function, thus jeopardizing human health. Myocardial infarction is accompanied by prolonged coronary occlusion, usually by cardiocyte apoptosis and necrosis, mass inflammatory cell infiltration and myocardial fibrosis, which induce myocardial injury. Myocardial infarction injury tends to cause cardiac dysfunction, thus affecting human health.

The present invention is based on a scientific discovery that NRG is critical to cardiac development and also plays a very important role in maintaining the cardiac function of adults; the present invention is based on a scientific discovery that NRG can strengthen the formation of myocardial cell sarcomeres, cytoskeleton and intercellular junction; the present invention is based on a scientific discovery that NRG can enhance the cardiac function of the animals or patients with heart failure in various animal models and clinical trials; the present invention is based on a scientific discovery that NRG exerts a protective effect on brain cells in an animal model of cerebral ischemia-reperfusion; the present invention is based on a scientific discovery that NRG exerts a protective effect on brain cells in an animal model of cardiac ischemia-reperfusion; NRG, NRG polypeptides and NRG mutants or other complexes with the NRG-like function are all within the scope of the present invention.

In the first aspect, the prevention invention provides a pharmaceutical preparation for preventing, treating or relieving myocardial injury in mammals. The prevention invention further provides a pharmaceutical preparation for preventing, treating or relieving myocardial infarction injury in mammals, and the mammals are preferably humans. The pharmaceutical preparation contains an effective amount of NRG or its functional fragments, or a nucleic acid encoding NRG or its functional fragments, or a substance that increases the production and/or function of NRG, and a pharmaceutically acceptable carrier, excipient, etc. The pharmaceutical preparation can be used in combination with other drugs or therapies for preventing, treating or relieving myocardial injury. In one embodiment, the pharmaceutical preparation containing NRG is effective in increasing the EF value of the mammalian left ventricle. In another embodiment, the pharmaceutical preparation containing NRG is effective in reducing the left ventricular end-diastolic volume (LVEDV) or left ventricular end-systolic volume (LVESV). In another embodiment, the pharmaceutical preparation containing NRG is subcutaneously injected via a syringe or another device. In another embodiment, the pharmaceutical preparation containing NRG is subcutaneously injected via a pump, such as an injection pump. In some embodiments, the syringe pump is a micropump. In a further embodiment, the micropump is an insulin pump. It is worth mentioning that the present invention is suitable for any pharmaceutically available preparation, and the pharmaceutical preparation contains the NRG described above or contains NRG and a pharmaceutically acceptable excipient, diluent or carrier. The pharmaceutical preparation used in the present invention includes but is not limited to the content of the present application.

In the second aspect, the present invention provides a method for preventing, treating or relieving myocardial injury in mammals. The present invention further provides a method for preventing, treating or relieving myocardial infarction injury in mammals, and the mammals are preferably humans. The method comprises the use of an effective amount of NRG or its functional fragments, or a nucleic acid encoding NRG or its functional fragments, or a substance that increases the production and/or function of NR required for preventing, treating or relieving myocardial injury in mammals. Other drugs can be used in combination with the method, in particular an effective amount of NRG or its functional fragments, or a nucleic acid encoding NRG or its functional fragments, or a substance that increases the production and/or function of NR for preventing, treating or relieving myocardial injury in mammals.

In the third aspect, the present invention provides a composition for preventing, treating or relieving myocardial injury in mammals. The present invention further provides a pharmaceutical composition for preventing, treating or relieving myocardial infarction injury in mammals, and the mammals are preferably humans. The pharmaceutical composition contains a type of NRG provided by the present invention for preventing, treating or relieving myocardial injury in mammals, and other drugs for preventing, treating or relieving myocardial injury. The pharmaceutical composition comprises an EGF-like domain, and the domain has been proven to be able to bind to and activate the receptors. In particular, as an example, but not for the purpose of limitation, the NRG provided by the present invention is a fragment of the NRG-1β2 isomer, and it comprises 177-237 amino acid. The amino acid sequence of the fragment is as follows:

```
                                           (SEQ ID NO: 1)
SHLVKCAEKEKTFCVNGGECFMVKDLSNPSRYLCKCPNEFTGDRCQNYVM

ASFYKAEELYQ.
```

In the fourth aspect, the present invention provides an administered dose of the pharmaceutical preparation containing NRG used for preventing, treating or relieving myocardial injury in mammals. The present invention further provides an administered dose of the pharmaceutical preparation containing NRG used for preventing, treating or relieving myocardial infarction injury in mammals, and the mammals are preferably humans. The effective dose means that one or more beneficial effects can be achieved when the dose of NRG is applied to a mammal. The beneficial effects can improve the cardiac function of patients with myocardial injury, or prevent further deterioration of their cardiac function, or suppress the deterioration of cardiac dysfunction that may be caused by myocardial injury. The dose provided by the present invention for a mammal is from 0.1 μg/kg/day (protein/body weight) to 360 μg/kg/day (protein/body weight). In one embodiment, the dose is from 0.3 μ/kg/day (protein/body weight) to 50 μg/kg/day (protein/body weight); in one embodiment, the effective dose is 7.5 μg/kg/day; in one embodiment, the effective dose is 15 μg/kg/day; in another embodiment, the effective dose is 30 μg/kg/day.

In the fifth aspect, the present invention provides a method of administration of the pharmaceutical preparation containing NRG for preventing, treating or relieving myocardial injury in mammals. The present invention further provides a method of administration of the pharmaceutical preparation containing NRG for preventing, treating or relieving myocardial infarction injury in mammals, and the mammals are preferably humans. The pharmaceutical preparation can be taken by oral administration, rectal administration, topical administration, inhalation administration, buccal administration (e.g. sublingual administration), parenteral administration (e.g. subcutaneous injection, intramuscular injection, intracutaneous injection or intravenous injection), transdermal administration or other proper methods. In one embodiment, NRG is administered only once a day. In another embodiment, NRG is administered multiple times a day. In one embodiment, NRG is administered in one day. In another embodiment, this tolerance dose of NRG is administered within a few days. In another embodiment, NRG is administered multiple times a day, for many consecutive days. In another embodiment, NRG is administered 2 days a week, multiple times a day, for many consecutive weeks. In another embodiment, NRG is injected subcutaneously 2 days a week, 3 times a day, for many consecutive weeks. In another embodiment, NRG is injected subcutaneously 3 times a day, for many for consecutive days. In another embodiment, NRG is injected subcutaneously 3 times a day, for 35 consecutive days. In another embodiment, NRG is injected subcutaneously 3 times a day, for 38 consecutive days. In another embodiment, NRG is injected subcutaneously 3 times a day, for 49 consecutive days. In another embodiment, NRG is injected subcutaneously 3 times a day, for 60 consecutive days. In another embodiment, NRG is injected subcutaneously 3 times a day, for more than 35 consecutive days. In another embodiment, NRG is administered multiple times a day, for many consecutive days, followed by slow withdrawal. In another embodiment, NRG is administered multiple times a day, for many consecutive days, followed by three-week slow withdrawal: administered every other day in the first week; administered every three days in the second week; injected subcutaneously every four days in the third week. In another embodiment, NRG is injected subcutaneously 3 times a day, for more than 38 consecutive days, followed by slow withdrawal. In another embodiment, NRG is injected subcutaneously 3 times a day, for 49 consecutive days, followed by three-week slow withdrawal: administered every other day in the first week; administered every three days in the second week; injected subcutaneously every four days in the third week. In another embodiment, NRG is administered multiple times a day, for many consecutive days, followed by slow reduction in daily dose. In another embodiment, NRG is administered 3 times a day, for many consecutive days, followed by slow reduction in daily dose. In another embodiment, NRG is s injected subcutaneously 3 times a day, for more than 60 consecutive days, followed by slow reduction in daily dose. In another embodiment, NRG is injected subcutaneously 3 times a day, for 60 continuous days, followed by three-week slow withdrawal: the daily dose is half of the continuously administered dose in the first week; the daily dose is a quarter of the continuously administered dose in the second week; the daily dose is one eighth of the continuously administered dose in the third week.

The present invention also provides a kit for preventing, treating or relieving myocardial injury in mammals. The present invention also provides a kit for preventing, treating or relieving myocardial infarction injury in mammals, and the mammals are preferably humans. The kit contains a single dose or multiple doses of the aforesaid pharmaceutical preparation or composition for preventing, treating or relieving myocardial injury, and instructions on how to use the pharmaceutical preparation or composition.

The pharmaceutical preparation or composition provided by the present invention can be administered before, during or after the occurrence of a cardiac disease. When used for prevention, the pharmaceutical preparation or composition is generally administered before the occurrence of the cardiac disease. When used for treatment, the pharmaceutical preparation or composition is generally administered during or after the occurrence of the cardiac disease. In one embodiment, the pharmaceutical preparation or composition provided by the present invention is administered before the occurrence of the cardiac disease. In another embodiment, the pharmaceutical preparation or composition provided by the present invention is administered when myocardial infarction occurs. In another embodiment, the pharmaceutical preparation or composition provided by the present invention is administered after the occurrence of the cardiac disease.

The pharmaceutical preparation or composition provided by the present invention can be taken by oral administration, rectal administration, topical administration, inhalation administration, buccal administration (e.g. sublingual administration), parenteral administration (e.g. subcutaneous injection, intramuscular injection, intracutaneous injection or intravenous injection), transdermal administration or other proper methods. Subcutaneous injection can be performed using a syringe, a pump (a microinfusion pump) or another administration apparatus. The dosage forms of the pharmaceutical preparation or composition provided by the present invention include but are not limited to tablets, lozenges, cachets, dispersant, suspension liquid, solution, capsules, ointment and similar forms.

B. Definitions

Unless otherwise defined, all the scientific and technical terms used herein have the same meaning as is understood by those skilled in the art. All the patent documents, patent application documents, published patent documents and other publications are taken as reference. If any definition covered in the present section has a meaning different from what is explained in the aforesaid documents, the explanation given in the present section shall prevail.

Unless otherwise specified, "a/an", as used herein, means "at least one" or "one or more than one".

"Mammals", as used herein, refer to non-human primates (bovines, pigs, horses, cats, dogs, rats, mice, etc.) or primates (monkeys, humans), and are preferably humans.

"Myocardial injury", as used herein, refers to a type of myocardial damage caused by a pathological cardiac disease such as heart failure, myocardial infarction, coronary atherosclerotic heart disease, arrhythmia, myocardial disease, valvular heart disease, infective endocarditis, pericardial disease, ischemic heart disease or congenital heart disease. Myocardial injury tends to cause cardiac dysfunction, thereby affecting human health. The pathogenesis of myocardial damage is related to multiple pathophysiological changes, including the production of oxyradical, calcium overload, inflammatory reaction caused by neutrophil invasion into the injured area, cardiocyte apoptosis or necrosis, metabolic disorders of tissues caused by energy supply imbalance, abnormal cardiac signal transduction, cholesterol accumulation, and formation of atherosclerotic plaques.

"Neuregulin" or "NRG", as used herein, refers to a protein or polypeptide that can bind to and activate ErbB2, ErbB3, ErbB4 or a heterodimer or homodimer. It includes the NRG isoforms, the EGF-like domain in NRG, the polypeptides containing the EGF-like domain of NRG, NRG mutants or derivatives, and other gene products of NRG that are capable of activating the above-mentioned receptors. NRG also includes NRG-1, NRG-2, NRG-3 and NRG-4, polypeptides, fragments, and complexes with the NRG-like function. Preferably, NRG is a type of protein or polypeptide that can bind to and activate ErbB2/ErbB4 or ErbB2/ErbB3 heterodimers. As an example, but not for the purpose of limitation, the NRG (rhNRG) provided by the present invention is a fragment of the NRG-1β2 isomer, i.e., 177-237 amino acid fragment, which contains an EGF-like domain. The amino acid sequence of the fragment is as follows:

```
(SEQ ID NO: 1)
SHLVKCAEKEKTFCVNGGECFMVKDLSNPSRYLCKCPNEFTGDRCQNYVM

ASFYKAEELYQ.
```

The NRG used in the present invention can activate the aforesaid receptors and regulate their biological functions, e.g. it can stimulate skeletal muscle cells to synthesize an acetylcholine receptor; promote the differentiation, survival and DNA synthesis of cardiocytes. NRG also comprises the conservative NRG mutants that do not substantially affect its biological functions. As is clear to those skilled in the art, the mutation of a single amino acid in a non-critical zone does not cause a change in the biological functions of the protein or polypeptide (Watson et al., Molecular Biology of the Gene, 4th Edition, 1987, The Bejacmin/Cummings Pub. co., p. 224). The NRG used in the present invention can be extracted from natural resources or obtained by recombinant technology, artificial synthesis or other means.

"EGF-like domain", as used herein, refers to polypeptide fragment encoded by the NRG gene that can bind to and activate ErbB2, ErbB3, ErbB4 or its heterodimer or homodimer, and has a structure similar to the EGF receptor binding zone described in the literature below: WO 00/64400; Holmes et al., Science, 256: 1205-1210 (1992); U.S. Pat. Nos. 5,530,109 and 5,716,930; Hijazi et al., Int. J. Oncol., 13: 1061-1067 (1998); Chang et al., Nature, 387: 509-512 (1997); Carraway et al., Nature, 387: 512-516 (1997); Higashiyama et al., J. Biochem., 122: 675-680 (1997); and WO 97/09425. In some embodiments, the EGF-like domain binds to and activates ErbB2/ErbB4 or ErbB2/ErbB3 heterodimers. In some embodiments, the EGF-like domain comprises the amino acids in the receptor binding zone of NRG-1. In some embodiments, the EGFP-like domain refers to the 177-226, 177-237 or 177-240 amino acid of NRG-1. In some embodiments, the EGFP-like domain comprises the amino acids in the receptor binding zone of NRG-2. In some embodiments, the EGF-like domain comprises the amino acids in the receptor binding zone of NRG-3. In some embodiments, the EGF-like domain comprises the amino acids in the receptor binding zone of NRG-4. In some embodiments, the EGF-like domain comprises the amino acid sequence described in U.S. Pat. No. 5,834,229: AlaGluLysGlu Lys Thr Phe Cys Val Asn Gly Gly Glu Cys Phe Met Val Lys Asp Leu Ser Asn Pro.

NRG can be made into an agent that can be taken by oral administration, rectal administration, topical administration, inhalation administration, buccal administration (e.g. sublingual administration), parenteral administration (e.g. subcutaneous injection, intramuscular injection, intracutaneous injection or intravenous injection), transdermal administration or other proper methods. In all modes of administration, the most suitable route of administration needs to be selected according to the treatment conditions and severity, as well as the properties of the specific NRG used. NRG can be administered alone. Or more suitably, NRG can be administered with some pharmaceutically acceptable carriers or excipients. Any suitable, pharmaceutically acceptable carrier or excipient applies to the current method (Remington: The Science and Practice of Pharmacy, Alfonso R. Gennaro (Editor) Mack Publishing Company, April 1997).

The "pump" used herein is an administration apparatus for subcutaneous injection of a pharmaceutical liquid, drug, protein and/or other compositions. It can be used for continuous, accurate and quantitative administration. The pump is provide with a subcutaneous catheter for continuous subcutaneous infusion. The catheter can be placed externally or the catheter port can be embedded in the pump mechanism. The microinfusion pump is portable and easy-to-use device that can be used for accurate infusion. For example, an insulin pump is a medical device used to administer insulin or other drugs during the treatment of diabetes or other diseases. It is also considered to be used for continuous subcutaneous insulin delivery. The insulin pump can be equipped with a disposable thin-walled plastic pipe or a catheter so that insulin or other drugs can enter the tissues. The catheter can be inserted subcutaneously and translocated as needed. The pump can be mounted in an external device that can be connected to the patient, or in a device that can be implanted in the patient's body. An external pump refers to a device designed for use in a fixed location such as a hospital, a clinic or a similar place, in particular referring to a mobile or portable device, such as a pump that can be carried by a patient or a similar device. The external pump comprises reservoir capable of storing a fluid medium, such as but not limited to a fluid medium containing NRG.

The external pump can be connected to the patient through flowing liquid, e.g. through a proper hollow tube. The hollow tube can be connected with a hollow needle, which is used to pierce the patient's skin for infusion. Alternatively, the hollow tube can be directly connected to the patient through a cannula or a similar object. The external pump can be worn by the patient or attached to or underneath the patient's clothes. An appropriate pump refers to but is not limited to a microinfusion pump that can be used for high-frequency infusion, such as the MiniMedParadigm522 insulin pump, MiniMedParadigm722 insulin pump, MiniMedParadigm515 insulin pump, MiniMedParadigm715 insulin pump, MiniMedParadigm512R insulin pump, MiniMedParadigm712R insulin pump, MiniMedParadigm508 insulin pump, and MiniMedParadigm508R insulin pump (Medtronic, Northridge, Canada), and other similar devices well-known to those skilled in the art.

The examples of administration apparatuses like an external pump described in U.S. patent Ser. No. 11/211,095 (date of application: Aug. 23, 2005, publication No.: US2006/0264894, authorization No.: U.S. Pat. No. 7,686,787) and published PCT applications WO01/70307 (PCT/US01/09139), WO04/030716 (PCT/US2003/028769), WO04/030717 (PCT/US2003/029019) and WO2013075622 (PCT/CN2012/0849 36), US Patent US2005/0065760 (Method for Advising Patients Concerning Doses of Insulin) and U.S. Pat. No. 6,589,229 (Wearable Self-Containing Drug Infusion Device) are cited here.

As use herein, "other drugs or therapies that can be used to prevent, treat or relieve myocardial injury" refer to the drugs and interventional therapies that are proverbially applicable to the treatment of myocardial injury, as well as the drugs and interventional therapies that are proverbially applicable to the treatment of myocardial infarction injury. Among them, the drugs for treating myocardial infarction include antiplatelet drugs (aspirin, clopidogrel, etc.), anticoagulants (heparin, bivalirudin, etc.), thrombolytic agents (alteplase, tenecteplase, urokinase, recombinant human prourokinase, etc.), lipid-lowering agents (statins, cholesterol absorption inhibitors), angiotensin converse enzyme inhibitors/ANG II receptor blockers, β receptor blockers, calcium channel blockers, nitric acid esters, phosphatase inhibitors, diuretics, renin-angiotensin-aldosterone system (RAS) antagonists, myocardial energy optimizers, drugs for improving ischemic tissue metabolism, free radical scavengers, etc. The interventional therapies include coronary interventional therapy, etc.

BRIEF DESCRIPTION OF THE DRAWINGS

FIG. 1 shows the echocardiographic results of the effect of NRG in treating rats with acute myocardial infarction through long-term subcutaneous administration of different doses FIG. 2 shows the echocardiographic results of the effect of NRG in treating rats with acute myocardial infarction through long-term subcutaneous administration at different frequencies FIG. 3 shows the therapeutic effect of NRG on acute myocardial infarction in rats through long-term subcutaneous administration followed by withdrawal through frequency reduction FIG. 4 shows the therapeutic effect of NRG on acute myocardial infarction in rats through long-term subcutaneous administration followed by withdrawal through dose reduction

EXAMPLES

Example 1: Therapeutic Effect of rhNRG on Acute Myocardial Infarction in Rats Through Long-Term Subcutaneous Administration of Different Doses—a Study on the Dose-Effect Relationship of NRG

1. Objective

To investigate the dose-effect relationship of NRG for treatment of acute myocardial infarction in rats by observing the therapeutic effect of different doses of rhNRG on acute myocardial infarction in rats in a rat model of myocardial infarction caused by left coronary artery ligation.

2. Experimental Drugs 2.1 Excipient: Developed by Zensun (Shanghai) Sci & Tech Co., Ltd.
2.2 rhNRG: Developed by Zensun (Shanghai) Sci & Tech Co., Ltd.

3. Experimental Animals 3.1 Strain and Source: Wistar Rats, Provided by Shanghai Sippe-Bk Lab Animal Co., Ltd.
3.2 Gender, Body Weight and Certificate: Male, 200-270 g

4. Experimental Materials and Equipment

An anesthesia apparatus, an isoflurane evaporator, from MSS INTERNATIONAL LTD.
Isoflurane 100 ml/bottle, from RWD Life Technologies Co., Ltd.
A cardiac ultrasonic detector Vivid E95
Ningbo Lingqiao suture needle with threads, from Ningbo Medical Needle Co., Ltd.

5. Experimental Methods 5.1 Establishment of a Rat Model of Heart Failure Caused by Coronary Artery Ligation
The rats were anesthetized with isoflurane through a gaseous anesthesia apparatus. Then, the rats were fixed in a supine position. After chest hair removal, the skin was disinfected with 75% alcohol. After the incision of the left anterior chest skin, the thoracic muscles were bluntly separated, with the $4^{th}$ and $5^{th}$ ribs exposed. Hemostatic forceps were used to bluntly cut off the muscle between the $4^{th}$ and $5^{th}$ ribs. Both hands were used to squeeze the heart out of the thoracic cavity so that the heart should be fully exposed for observation of lung inflation and heartbeats. The left atrial appendage and pulmonary conus were fully exposed to ligate the left anterior descending coronary artery (LADCA) with surgical suture between them. The heart was quickly restored upon after ligation. Then, the thoracic muscles and skin were sutured. After surgery, the rats were put back into the cages for feeding and close observations.

5.2 Grouping and Administration

TABLE 1

| | | | Frequency and |
| --- | --- | --- | --- |
| | Administered | Route of | Cycle of |
| Group | Dose | Administration | Administration |
| Control Group | — | Subcutaneous injection | 3 times a day × 60 days |
| High-dose NRG | 15 μg/kg/D | Subcutaneous injection | 3 times a day × 60 days |
| Middle-dose NRG | 7.5 μg/kg/D | Subcutaneous injection | 3 times a day × 60 days |
| Low-dose NRG | 3.75 μg/kg/D | Subcutaneous injection | 3 times a day × 60 days |

Administration began on the day following the animal model establishment of myocardial infarction.

5.3 Observation Indexes
After being anesthetized with 4% isoflurane, the rats were fixed onto the operating board in the left lateral recumbent position. The head of the rats was fixed in the breathing mask of the gaseous anesthesia machine, with isoflurane used for maintenance of anesthesia. After chest hair removal, the skin was disinfected with 75% alcohol and coated with a coupling agent. An echocardiography probe was used to detect any echo signal from the left ventricle of the rats. The left ventricular end-diastolic diameter and left ventricular end-systolic diameter (D) were measured. The left ventricular end-diastolic volume (EDV) and end-systolic volume (ESV) were calculated. Also, the ejection fraction (EF) value was found, EF=(EDV−ESV)/EDV*100%.

5.3.2 Data Processing
All experimental data were expressed in ±SD.

6. Experimental Results 6.1 Echocardiographic Results
Echocardiography was performed after 60 days of continuous NRG administration. The results showed that the LVEDd, LVEDs and EF value of the excipient group were 0.971±0.07 cm, 0.832±0.08 cm and 34.6±7.00%, respectively; the LVEDd, LVEDs and EF value of the 15 μg/kg-NRG group were 0.975±0.07 cm, 0.794±0.10 cm and 42.9±11.32%, respectively; the LVEDd, LVEDs and EF value of the 7.5 μg/kg-NRG group were 0.965±0.07 cm, 0.808±0.11 cm and 38.4±12.17%, respectively; the LVEDd, LVEDs and EF value of the 3.75 μg/kg-NRG group were 0.994±0.08 cm, 0.839±0.12 cm and 37.0±12.23%, respectively. According to the data of LVEDd and LVEDs, the LVEDd and LVEDs of the high-dose NRG group could be reduced. According to the data of EF value, the cardiac function of the rats in the high-dose, middle-dose and low-dose groups was all improved after 60 days of continuous administration, and there was dose-effect relationship among the three groups. See Table 2 and FIG. 1 for details.

TABLE 2

Echocardiographic results of the effect of NRG in treating rats with acute myocardial infarction
through 60-day subcutaneous administration of different doses ( $\bar{x}$ ± SD)

| Time | Dose (μg/kg) | Group | Number of animals | LVEDd (cm) | LVEDs (cm) | EF (%) |
|---|---|---|---|---|---|---|
| DAY 20 | — | Excipient | 15 | 0.903 ± 0.06 | 0.762 ± 0.08 | 37.1 ± 8.27 |
| | 15 | NRG | 18 | 0.908 ± 0.05 | 0.759 ± 0.08 | 40.6 ± 9.15 |
| | 7.5 | NRG | 16 | 0.924 ± 0.05 | 0.756 ± 0.08 | 41.9 ± 15.17 |
| | 3.75 | NRG | 13 | 0.937 ± 0.06 | 0.777 ± 0.08 | 39.7 ± 10.84 |
| DAY 40 | — | Excipient | 15 | 0.953 ± 0.06 | 0.807 ± 0.09 | 36.4 ± 10.24 |
| | 15 | NRG | 18 | 0.946 ± 0.08 | 0.775 ± 0.11 | 42.2 ± 11.27 |
| | 7.5 | NRG | 16 | 0.946 ± 0.08 | 0.782 ± 0.12 | 40.5 ± 13.39 |
| | 3.75 | NRG | 13 | 0.982 ± 0.09 | 0.813 ± 0.13 | 40.4 ± 12.86 |
| DAY 60 | — | Excipient | 15 | 0.971 ± 0.07 | 0.832 ± 0.08 | 34.6 ± 7.00 |
| | 15 | NRG | 18 | 0.975 ± 0.07 | 0.794 ± 0.10 | 42.9 ± 11.32 |
| | 7.5 | NRG | 16 | 0.965 ± 0.07 | 0.808 ± 0.11 | 38.4 ± 12.17 |
| | 3.75 | NRG | 13 | 0.994 ± 0.08 | 0.839 ± 0.12 | 37.0 ± 12.23 |

7. Conclusions

After 60-day treatment with rhNRG, the EF value of the treatment groups, which were subcutaneously injected with 5 μg/kg, 2.5 μg/kg, 1.25 μg/kg of NRG 3 times a day, was higher than that of the control group, and there was a certain dose-effect relationship for the three doses.

Example 2: Therapeutic Effect of rhNRG on Acute Myocardial Infarction in Rats Through Long-Term Subcutaneous Administration at Different Frequencies

1. Objective

To investigate the therapeutic effect of a certain dose of rhNRG on cute myocardial infarction in rats through long-term subcutaneous administration at different frequencies in a rat model of myocardial infarction caused by left coronary artery ligation.

2. Experimental Drugs 2.1 Excipient: Developed by Zensun (Shanghai) Sci & Tech Co., Ltd.
2.2 rhNRG: Developed by Zensun (Shanghai) Sci & Tech Co., Ltd.

3. Experimental Animals 3.1 Strain and Source: Wistar Rats, Provided by Shanghai Sippe-Bk Lab Animal Co., Ltd.
3.2 Gender, Body Weight and Certificate: Male, 200-270 g

4. Experimental Materials and Equipment

The same as "4. Experimental Materials and Equipment" in Example 1.

5. Experimental Methods 5.1 Establishment of a Rat Model of Heart Failure Caused by Coronary Artery Ligation
Established in the same way as the rat model of heart failure caused by coronary artery ligation in 5.1, Embodiment 1

5.2 Grouping and Administration

TABLE 3

Experimental animal grouping and administration schedule

| Group | Administered Dose | Route of Administration | Frequency and Cycle of Administration |
|---|---|---|---|
| Control Group | — | Subcutaneous injection | 3 times a day × 35 days |
| NRG/30 μg/kg/ Day | 30 μg/kg/ Day | Subcutaneous injection | 3 times a day × 35 days |
| NRG/30 μg/kg/ BIW | 30 μg/kg/ Day | Subcutaneous injection | 3 times a day, 2 days a week × 5 weeks |
| Nrg/30 μG/KG/ Day*7 + QW | 30 μg/kg/ Day + 30 μg/kg/ 7 days | Subcutaneous injection | 3 times a day × 7 days once a day, 1 day/week × 4 weeks |

All the experimental animals were randomly divided into groups upon coronary artery ligation. According to post-ligation survival, the rats were randomly divided into 4 groups by body weight: the excipient group (control group), the NRG30 μg/kgDay group, the NRG30 μg/kg/BIW group and the NRG30 μgkgDay*7+QW group. Administration began on the day following the animal model establishment of myocardial infarction. For the first three groups and for the fourth group on the first 7 days, the rats were given subcutaneous injection 3 times a day and weighed once a day. They took medicine by weight and the dose was 30 μg/kg/day. For the fourth group in the last four weeks, the rats were injected with NRG on one day per week, and the daily dose was 30 μg/kg.
5.3 Observation Indexes
5.3.1 Cardiac Function Test
After being anesthetized with 4% isoflurane, the rats were fixed onto the operating board in the left lateral recumbent position. The head of the rats was fixed in the breathing mask of the gaseous anesthesia machine, with isoflurane used for maintenance of anesthesia. After chest hair removal, the skin was disinfected with 75% alcohol and coated with a coupling agent. An echocardiography probe was used to detect any echo signal from the left ventricle of the rats. The left ventricular end-diastolic diameter and left ventricular end-systolic diameter (D) were measured. The left ventricular end-diastolic volume (EDV) and end-systolic volume (ESV) were calculated. Also, the ejection fraction (EF) value was found, EF–(EDV–ESV)/EDV*100%. The cardiac function of the rats was performed by echocardiography in the $1^{st}$, $2^{nd}$, $3^{rd}$ and $5^{th}$ weeks after the occurrence of myocardial infarction.

5.3.2 Data Processing

All experimental data were expressed in ±SD.

6. Experimental Results 6.1 Echocardiographic Results

Echocardiography was performed after 35 consecutive days of NRG administration. The LVEDd, LVEDs, EF value of the control group were 0.925±0.084 cm, 0.756±0.107 cm and 42.5±10.174%, respectively; the LVEDd, LVEDs, EF value of the NRG/30 µg/kg/Day group were 0.879±0.058 cm, 0.694±0.077 cm and 47.9±8.342%, respectively; the LVEDd, LVEDs, EF value of the NRG/30 µg/kg/BIW group were 0.928±0.084 cm, 0.746+0.110 cm and 45.2+10.248%, respectively; the LVEDd, LVEDs, EF value of the NRG/30 µg/kg/Day*7+QW group were 0.931±0.070 cm, 0.760±0.097 cm and 42.7±9.892%, respectively.

After 35 days of continuous administration, as shown by the data of LVEDd and LVEDs, NRG/30 µg/kg/Day could significantly reduce the LVEDd and LVEDs; according to the data of EF value, it was significantly higher in the NRG/30 µg/kg/Day group than in the control group; it showed a rising trend in the NRG/30 µg/kg/BIW group compared with the control group; compared with the control group, the cardiac function of the rats in the NRG/30 µg/kg/Day*7+QW group was improved to some extent on the first 7 days of continuous administration, i.e., it showed a rising trend. Then, an injection was given every 7 days to maintain the efficacy. See Table 4 and FIG. 2 for the results.

2. Experimental Drugs 2.1 Excipient: Developed by Zensun (Shanghai) Sci & Tech Co., Ltd.

2.2 rhNRG: Developed by Zensun (Shanghai) Sci & Tech Co., Ltd.

3. Experimental Animals 3.1 Strain and Source: Wistar Rats, Provided by Shanghai Sippe-Bk Lab Animal Co., Ltd.

3.2 Gender, Body Weight and Certificate: Male, 200-270 g

4. Experimental Materials and Equipment

The same as "4. Experimental Materials and Equipment" in Embodiment 1

5. Experimental Methods 5.1 Establishment of a Rat Model of Heart Failure Caused by Coronary Artery Ligation Established in the same way as the rat model of heart failure caused by coronary artery ligation in 5.1, Embodiment 1

5.2 Grouping and Administration

The rats were randomly divided into groups and medicated upon coronary artery ligation. According to post-ligation survival, the rats were randomly divided into two groups, including the excipient group and the NRG30 µg/kg group. There were 19 rats in the excipient group and there

TABLE 4

Echocardiographic results of the therapeutic effect of NRG on myocardial infarction
in rats through long-term subcutaneous administration at different frequencies ($\bar{x}$ ± SD)

| Time | Group | Number of animals | LVEDd (cm) | LVEDs (cm) | EF (%) |
|------|-------|-------------------|------------|------------|--------|
| DAY 8 | Control Group | 52 | 0.800 ± 0.060 | 0.629 ± 0.074 | 48.6 ± 7.992 |
| | NRG/30 µg/kg/Day | 48 | 0.785 ± 0.046 | 0.601 ± 0.063 | 52.2 ± 7.802 |
| | NRG/30 µg/kg BIW | 48 | 0.809 ± 0.045 | 0.625 ± 0.068 | 50.9 ± 8.958 |
| | NRG/30 µg/kg Day*7 + QW | 50 | 0.785 ± 0.045 | 0.607 ± 0.061 | 50.9 ± 7.337 |
| DAY 15 | Control Group | 50 | 0.863 ± 0.058 | 0.696 ± 0.081 | 44.6 ± 9.297 |
| | NRG/30 µg/kg/Day | 47 | 0.832 ± 0.054 | 0.646 ± 0.075 | 50.3 ± 8.49 |
| | NRG/30 µg/kg BIW | 48 | 0.856 ± 0.065 | 0.671 ± 0.091 | 48.9 ± 9.893 |
| | NRG/30 µg/kg Day*7 + QW | 50 | 0.864 ± 0.054 | 0.686 ± 0.074 | 47.1 ± 8.344 |
| DAY 22 | Control Group | 50 | 0.898 ± 0.070 | 0.728 ± 0.090 | 43.8 ± 8.854 |
| | NRG/30 µg/kg/Day | 46 | 0.859 ± 0.057 | 0.670 ± 0.069 | 49.5 ± 7.897 |
| | NRG/30 µg/kg BIW | 48 | 0.896 ± 0.074 | 0.711 ± 0.102 | 47.1 ± 10.427 |
| | NRG/30 µg/kg Day*7 + QW | 50 | 0.905 ± 0.062 | 0.729 ± 0.08 | 44.7 ± 8.434 |
| DAY 36 | Control Group | 50 | 0.925 ± 0.084 | 0.756 ± 0.107 | 42.5 ± 10.174 |
| | NRG/30 µg/kg/Day | 46 | 0.879 ± 0.058 | 0.694 ± 0.077 | 47.9 ± 8.342 |
| | NRG/30 µg/kg BIW | 48 | 0.928 ± 0.084 | 0.746 ± 0.110 | 45.2 ± 10.248 |
| | NRG/30 µg/kg Day*7 + QW | 50 | 0.931 ± 0.070 | 0.76 ± 0.097 | 42.7 ± 9.892 |

Example 3: Therapeutic Effect of rhNRG on Acute Myocardial Infarction in Rats Through Long-Term Subcutaneous Administration Followed by Withdrawal Through Frequency Reduction

1. Objective

To observe the therapeutic effect of rhNRG on acute myocardial infarction in rats through long-term administration followed by withdrawal through frequency reduction in a rat model of myocardial infarction caused by left coronary artery ligation.

were 18 rats in the NRG group. Continuous administration of medicine started on the day following the modeling, with subcutaneous administration for 3 times a day, at a dose of 10 µg/kg. Echocardiography was performed on day 14 after modeling. All the animals were medicated continuously until day 38, and the animals in the NRG group were examined by echocardiography. The animals in the NRG group were averagely divided into two subgroups, with the animals in one subgroup continuing to be medicated while the animals in the other subgroup stopped taking medicine at an early stage. The excipient group continued to be medicated. For the continuous NRG administration subgroup, a 3-week withdrawal plan was implemented on day 49: medicated every other day in the first week; medicated every three days in the second week; subcutaneously injected with NRG every four days in the third week. In terms of administration method, the rats were subcutaneously injected with NRG 3 times a day, exactly the same as above. For the NRG withdrawal subgroup, the clinical symptoms of the rats were observed. All the animals underwent echocardiography every week for monitoring of the changes in the cardiac function.

5.3 Observation Indexes 5.3.1 Cardiac Function Test

After being anesthetized with 4% isoflurane, the rats were fixed onto the operating board in the left lateral recumbent position. The head of the rats was fixed in the breathing mask of the gaseous anesthesia machine, with isoflurane used for maintenance of anesthesia. After chest hair removal, the skin was disinfected with 75% alcohol and coated with a coupling agent. An echocardiography probe was used to detect any echo signal from the left ventricle of the rats. The left ventricular end-diastolic diameter and left ventricular end-systolic diameter (D) were measured. The left ventricular end-diastolic volume (EDV) and end-systolic volume (ESV) were calculated. Also, the ejection fraction (EF) value was found, $EF=(EDV-ESV)/EDV*100\%$.

5.3.2 Data Processing

All experimental data were expressed in $\pm SD$. GraphPad Prism6 was used for one-way ANOVA analysis. $P<0.05$ indicates a significant inter-group difference; $P<0.01$ indicates an extremely significant inter-group difference.

6. Experimental Results 6.1 Echocardiographic Results

Echocardiography was performed after 35 consecutive days of NRG administration. The LVEDd, LVEDs and EF value of the excipient group were 0.988±0.08 cm, 0.850±0.10 cm and 33.6±11.36%, respectively; the LVEDd, LVEDs and EF value of the NRG group were 0.953±0.05 cm, 0.767±0.06 cm and 44.9±6.09%, respectively; the results showed that NRG could significantly reduce the LVEDd and LVEDs and strengthen the cardiac systolic function, thereby reversing left ventricular remodeling; after 49 days of continuous administration, the LVEDd, LVEDs and EF value of the excipient group were 1.020±0.10 cm, 0.881±0.15 cm and 33.1±14.55%, respectively; the LVEDd, LVEDs and EF value of the NRG withdrawal subgroup were 0.987±0.05 cm, 0.807±0.06 cm and 42.2±5.48%, respectively, while the LVEDd, LVEDs and EF value of the continuous NRG administration subgroup were 0.973±0.07 cm, 0.783±0.08 cm and 45.0±5.51%, respectively; the results showed that the sudden withdrawal of NRG exerted some effect on the cardiac function of the rats. A gradual withdrawal plan was implemented in the continuous NRG administration subgroup, and echocardiography was performed in the second week after drug withdrawal. The LVEDd, LVEDs and EF value of the early NRG withdrawal subgroup were 1.043±0.06 cm, 0.887±0.06 and 35.4±6.78%, respectively; the LVEDd, LVEDs and EF value of the gradual NRG withdrawal subgroup were 0.989±0.07 cm, 0.814±0.08 and 41.3±4.92%, respectively. There was a significant difference from the excipient group. Echocardiography was performed in the third week after withdrawal. The LVEDd, LVEDs and EF value of the early NRG withdrawal subgroup were 1.010±0.06 cm, 0.842+0.06 cm and 38.9±5.04%, respectively; the LVEDd. LVEDs and EF value of the gradual NRG withdrawal subgroup were 0.976±0.06 cm, 0.805±0.07 cm, 40.8±4.67%, respectively. Compared with the excipient group, the effect of gradual withdrawal of NRG on the cardiac function of the rats was allayed. See Tables 5 & 6 and FIG. 3 for the results.

TABLE 5

Echocardiographic results of the effect of NRG in treating rats with myocardial infarction through 35-day subcutaneous administration ($\bar{x} \pm SD$)

| Time | Dose (μg/kg) | Group | Number of animals | LVEDd (cm) | LVEDs (cm) | EF (%) |
|---|---|---|---|---|---|---|
| DAY 14 | — | Excipient | 16 | 0.878 ± 0.05 | 0.740 ± 0.08 | 37.1 ± 11.11 |
| | 30 | NRG | 18 | 0.860 ± 0.04 | 0.694 ± 0.06 | 44.5 ± 7.85* |
| DAY 21 | — | Excipient | 16 | 0.941 ± 0.06 | 0.801 ± 0.09 | 35.4 ± 11.91 |
| | 30 | NRG | 18 | 0.905 ± 0.04 | 0.725 ± 0.06* | 45.5 ± 7.96** |
| DAY 28 | — | Excipient | 16 | 0.961 ± 0.97 | 0.832 ± 0.11 | 32.4 ± 13.34 |
| | 30 | NRG | 18 | 0.928 ± 0.05 | 0.749 ± 0.06** | 44.3 ± 6.95*** |
| DAY 35 | — | Excipient | 16 | 0.988 ± 0.08 | 0.850 ± 0.10 | 33.6 ± 11.36 |
| | 30 | NRG | 18 | 0.953 ± 0.05 | 0.767 ± 0.06** | 44.9 ± 6.09*** |

***$p < 0.001$ for the subgroups after treatment compared with the excipient group;

**$p < 0.01$ for the subgroups after treatment compared with the excipient group;

*$p < 0.05$ for the subgroups after treatment compared with the excipient group

TABLE 6

Echocardiographic results of the effect of NRG in treating rats with myocardial infarction in the two subgroups after 38-day subcutaneous administration ($\bar{x} \pm SD$)

| Time | Dose (μg/kg) | Group | Number of animals | LVEDd (cm) | LVEDs (cm) | EF (%) |
|---|---|---|---|---|---|---|
| DAY 38 | 30 | Administration | 9 | 0.953 ± 0.06 | 0.764 ± 0.07 | 44.9 ± 7.03 |
| | — | Withdrawal | 9 | 0.952 ± 0.05 | 0.767 ± 0.07 | 44.7 ± 6.26 |
| | — | Excipient | 16 | 1.005 ± 0.09 | 0.883 ± 0.11 | 29.8 ± 11.43 |

TABLE 6-continued

Echocardiographic results of the effect of NRG in treating rats with myocardial
infarction in the two subgroups after 38-day subcutaneous administration ($\bar{x} \pm$ SD)

| Time | Dose (µg/kg) | Group | Number of animals | LVEDd (cm) | LVEDs (cm) | EF (%) |
|------|------|------|------|------|------|------|
| DAY 42 | 30 | Administration | 8 | 0.948 ± 0.04 | 0.755 ± 0.04* | 46.5 ± 4.01*** |
| | — | Withdrawal | 9 | 0.969 ± 0.04 | 0.808 ± 0.05 | 39.1 ± 7.11* |
| | — | Excipient | 16 | 1.020 ± 0.10 | 0.881 ± 0.15 | 33.1 ± 14.55 |
| DAY 49 | 30 | Administration | 8 | 0.973 ± 0.07 | 0.783 ± 0.08* | 45.0 ± 5.51** |
| | — | Withdrawal | 9 | 0.987 ± 0.05 | 0.807 ± 0.06 | 42.2 ± 5.48* |
| | — | Excipient | 16 | 1.046 ± 0.08 | 0.920 ± 0.11 | 29.4 ± 10.34 |
| DAY 56 | 30 | Administration | 8 | 1.008 ± 0.06 | 0.843 ± 0.06* | 38.8 ± 3.78* |
| | — | Withdrawal | 9 | 1.031 ± 0.05 | 0.859 ± 0.07 | 39.0 ± 6.24* |
| | — | Excipient | 16 | 1.040 ± 0.11 | 0.907 ± 0.14 | 31.2 ± 12.43 |
| DAY 63 | 30 | Administration | 8 | 0.989 ± 0.07 | 0.814 ± 0.08* | 41.3 ± 4.92* |
| | — | Withdrawal | 9 | 1.043 ± 0.06 | 0.887 ± 0.06 | 35.4 ± 6.78 |
| | — | Excipient | 16 | 1.036 ± 0.10 | 0.905 ± 0.12 | 30.9 ± 9.23 |
| DAY 68 | 30 | Administration | 8 | 0.976 ± 0.06 | 0.805 ± 0.07 | 40.8 ± 4.67* |
| | — | Withdrawal | 9 | 1.010 ± 0.06 | 0.842 ± 0.06 | 38.9 ± 5.04* |
| | — | Excipient | 16 | 1.043 ± 0.11 | 0.920 ± 0.12 | 29.1 ± 9.63 |
| DAY 74 | 30 | Administration | 8 | 1.004 ± 0.05 | 0.842 ± 0.05* | 38.0 ± 3.81* |
| | — | Withdrawal | 9 | 1.060 ± 0.05 | 0.905 ± 0.05 | 34.6 ± 7.55 |

***$p < 0.001$ for the subgroups after treatment compared with the excipient group;
**$p < 0.01$ for the subgroups after treatment compared with the excipient group;
*$p < 0.05$ for the subgroups after treatment compared with the excipient group

7. Conclusions

Through long-term subcutaneous administration followed by withdrawal through frequency reduction, rhNRG can improve the cardiac function of the rats with myocardial infarction and reduce cardiac remodeling.

Example 4: Therapeutic Effect of rhNRG on Acute Myocardial Infarction in Rats Through Long-Term Subcutaneous Administration Followed by Withdrawal Through Dose Reduction

1. Objective

To observe the therapeutic effect of rhNRG on acute myocardial infarction in rats through long-term administration followed by withdrawal through frequency reduction in a rat model of myocardial infarction caused by left coronary artery ligation.

2. Experimental Drugs 2.1 Excipient: Developed by Zensun (Shanghai) Sci & Tech Co., Ltd.
2.2 rhNRG: Developed by Zensun (Shanghai) Sci & Tech Co., Ltd.

3. Experimental Animals 3.1 Strain and Source: Wistar Rats, Provided by Shanghai Sippe-Bk Lab Animal Co., Ltd.
3.2 Gender, Body Weight and Certificate: Male, 200-270 g

4. Experimental Materials and Equipment

The same as "4. Experimental Materials and Equipment" in Embodiment 1

5. Experimental Methods 5.1 Establishment of a Rat Model of Heart Failure Caused by Coronary Artery Ligation
Established in the same way as the rat model of heart failure caused by coronary artery ligation in 5.1, Embodiment 1
5.2 Grouping and Administration
5.3 Observation Indexes
The rats were randomly divided into groups and medicated upon coronary artery ligation. According to post-ligation survival, the rats were randomly divided into 2 groups by body weight. Subcutaneous injection was given 3 times a day, and the animals were weighed once a day. The animals were medicated by weight. Echocardiography was performed on day 10 after modeling. All the animals underwent echocardiography every 10 days, underwent echocardiography every week after dose reduction, and underwent echocardiography every 2 weeks after complete withdrawal. All the animals were medicated continuously till day 60, and then a three-week dose-reduction withdrawal plan was implemented: The administered dose was reduced to 15 µg/kg, 7.5 µg/kg and 3.75 µg/kg in the first, second and third week, respectively. The drug was completely withdrawn after three-week dose reduction to observe the clinical symptoms.
5.3.1 Cardiac Function Test
After being anesthetized with 4% isoflurane, the rats were fixed onto the operating board in the left lateral recumbent position. The head of the rats was fixed in the breathing mask of the gaseous anesthesia machine, with isoflurane used for maintenance of anesthesia. After chest hair removal, the skin was disinfected with 75% alcohol and coated with a coupling agent. An echocardiography probe was used to detect any echo signal from the left ventricle of the rats. The left ventricular end-diastolic diameter and left ventricular end-systolic diameter (D) were measured. The left ventricular end-diastolic volume (EDV) and end-systolic volume (ESV) were calculated. The ejection fraction (EF) value was found, EP=(EDV−ESV)/EDV*100%.

5.3.2 Data Processing

All experimental data were expressed in ±SD. GraphPad Prism6 was used for one-way ANOVA analysis. P<0.05 indicates a significant inter-group difference; P<0.01 indicates an extremely significant inter-group difference.

6. Experimental Results

6.1 Echocardiographic Results

Echocardiography was performed after 60 consecutive days of NRG administration. The LVEDd, LVEDs and EF of the excipient group were 1.048±0.07 cm, 0.910±0.09 cm and 32.1±6.6%, respectively; the LVEDd, LVEDs and EF of the NRG30 µg/kg/Day group were 0.981±0.08 cm, 0.794±0.08 cm and 43.8±8.0%, respectively. According to the data of LVEDd and LVEDs, the LVEDd and LVEDs of the everyday NRG administration group were significantly reduced, showing an extremely significant difference from the control group (p<0.001). According to the data of EF value, the EF value of the NRG group increased significantly after 60 days of continuous administration, showing an extremely significant difference from the control group (p<0.001). Frequency-unchanged and dose-reduction treatment was given 60 days later. Echocardiography was performed in the third week. The LVEDd, LVEDs and EF value of the control group were 1.038±0.07 cm, 0.899±0.10 cm and 32.4+9.5%, respectively; the LVEDd, LVEDs and EF value of the NRG/30 µg/kg/Day group were 0.981±0.08 cm, 0.799±0.08 and 42.3±11.2%. The drug was completely withdrawn after three-week dose reduction for an observation. The LVEDd, LVEDs and EF value of the control group were 1.065±0.07 cm, 0.942±0.10 cm and 28.3±9.4%, respectively; the LVEDd, LVEDs and EF value of the NRG/30 µg/kg/Day group were 0.994±0.08 cm, 0.826±0.10 cm and 39.3±12.7%, respectively. Echocardiography was performed in the ninth week after withdrawal. The LVEDd, LVEDs and EF value of the control group were 1.137±0.08 cm, 1.006±0.08 cm and 28.0+5.7%, respectively; the LVEDd, LVEDs and EF value of the NRG/30 µg/kg/Day group were NRG/30 µg/kg/day group was 1.104±0.08 cm, 0.950±0.09 cm, and 33.4±7.6%, respectively. Nine weeks after withdrawal, there remained a significant difference in LVEDd and LVEDs between the everyday NRG administration group and the control group; the EF value still showed a rising trend compared with the control group. See Table 7, 8, 9 and FIG. 4 for the results.

7. Conclusions

Given a certain dose and different frequencies of administration, rhNRG exerted some therapeutic effect on myocardial infarction in rats during continuous administration, enhancing the cardiac function of the rats with acute myocardial infarction and improving ventricular remodeling, and deferring aging caused by myocardial infarction. It still has a significant improving effect on the cardiac function of the rats with myocardial infarction a long time after withdrawal.

TABLE 7

Echocardiographic results of the effect of NRG in treating rats with myocardial infarction through 60-day subcutaneous administration ( $\bar{x}$ ± SD)

| Time | Dose (µg/kg) | Group | Number of animals | LVEDd (cm) | LVEDs (cm) | EF (%) |
|---|---|---|---|---|---|---|
| DAY 10 | — | Excipient | 17 | 0.840 ± 0.04 | 0.683 ± 0.05 | 43.5 ± 6.77 |
| | 30 | NRG/Day | 15 | 0.821 ± 0.05 | 0.637 ± 0.06 | 50.5 ± 4.96* |
| DAY 30 | — | Excipient | 16 | 0.940 ± 0.05 | 0.805 ± 0.06 | 34.4 ± 6.82 |
| | 30 | NRG/Day | 14 | 0.912 ± 0.06 | 0.725 ± 0.07* | 46.8 ± 6.37** |
| DAY 50 | — | Excipient | 16 | 0.995 ± 0.06 | 0.869 ± 0.08 | 30.9 ± 7.75 |
| | 30 | NRG/Day | 14 | 0.934 ± 0.07* | 0.754 ± 0.09*** | 44.4 ± 7.85*** |
| DAY 60 | — | Excipient | 16 | 1.048 ± 0.07 | 0.910 ± 0.09 | 32.1 ± 6.61 |
| | 30 | NRG/Day | 14 | 0.981 ± 0.08* | 0.794 ± 0.08*** | 43.8 ± 8.04*** |

***p < 0.001 for the subgroups after treatment compared with the excipient group;

**p < 0.01 for the subgroups after treatment compared with the excipient group;

*p < 0.05 for the subgroups after treatment compared with the excipient group

TABLE 8

Echocardiographic results of the effect of NRG in treating rats with myocardial infarction three weeks after dose reduction following 60-day subcutaneous administration ( $\bar{x}$ ± SD)

| Time | Dose (µg/kg) | Group | Number of animals | LVEDd (cm) | LVEDs (cm) | EF (%) |
|---|---|---|---|---|---|---|
| DAY 81 | — | Excipient | 16 | 1.038 ± 0.07 | 0.899 ± 0.10 | 32.4 ± 9.51 |
| | 30 | NRG/Day | 14 | 0.981 ± 0.07** | 0.799 ± 0.08*** | 42.3 ± 11.20** |

***p < 0.001 for the subgroups after treatment compared with the excipient group;

**p < 0.01 for the subgroups after treatment compared with the excipient group;

*p < 0.05 for the subgroups after treatment compared with the excipient group

TABLE 9

Echocardiographic results of the effect of NRG in treating rats with
myocardial infarction after withdrawal on day 81 of subcutaneous administration
($\bar{x} \pm$ SD)

| Time | Dose (μg/kg) | Group | Number of animals | LVEDd (cm) | LVEDs (cm) | EF (%) |
|------|--------------|-------|-------------------|------------|------------|--------|
| DAY 88 | — | Excipient | 17 | 1.065 ± 0.07 | 0.942 ± 0.10 | 28.3 ± 9.40 |
| | 30 | NRG/Day | 15 | 0.994 ± 0.08** | 0.826 ± 0.10*** | 39.3 ± 12.71*** |
| DAY 102 | — | Excipient | 16 | 1.072 ± 0.09 | 0.946 ± 0.13 | 29.0 ± 11.41 |
| | 30 | NRG/Day | 14 | 1.031 ± 0.07* | 0.872 ± 0.08* | 36.6 ± 7.69** |
| DAY 116 | — | Excipient | 16 | 1.107 ± 0.08 | 0.985 ± 0.12 | 27.2 ± 9.67 |
| | 30 | NRG/Day | 14 | 1.054 ± 0.07 | 0.908 ± 0.08** | 33.3 ± 5.12* |
| DAY 143 | — | Excipient | 14 | 1.137 ± 0.08 | 1.006 ± 0.08 | 28.0 ± 5.70 |
| | 30 | NRG/Day | 14 | 1.104 ± 0.08 | 0.950 ± 0.09 | 33.4 ± 7.60 |

***$p < 0.001$ for the subgroups after treatment compared with the excipient group;
**$p < 0.01$ for the subgroups after treatment compared with the excipient group;
*$p < 0.05$ for the subgroups after treatment compared with the excipient group

The invention claimed is:

1. A method for treating, or relieving myocardial injury in a mammal, comprising administering to the mammal an effective amount of neuregulin (NRG) at a dose of 2.5 μg/kg/day to 50 μg/kg/day multiple times a day for consecutive days, and following the administration slowly withdrawing the NRG through daily dose reduction within three weeks, wherein the daily dose is half of the administered dose in the first week; the daily dose is a quarter of the administered dose in the second week; and the daily dose is one eighth of the administered dose in the third week.

2. The method according to claim 1, wherein the NRG is NRG-1, NRG-2, NRG-3 or NRG-4.

3. The method according to claim 1, wherein the NRG is NRG-1.

4. The method according to claim 1, wherein the mammal is human.

5. A method for treating, or relieving myocardial injury in a mammal, comprising administering to the mammal neuregulin (NRG) at a dose of 2.5 μg/kg/day to 50 μg/kg/day multiple times a day for consecutive days, and following the administration slowly withdrawing the NRG through frequency reduction within three weeks comprising: administering the NRG every other day in the first week; administering the NRG every three days in the second week; and administering the NRG every four days in the third week.

6. The method according to claim 5, wherein the NRG is NRG-1, NRG-2, NRG-3 or NRG-4.

7. The method according to claim 5, wherein the NRG is NRG-1.

8. The method according to claim 5, wherein the mammal is human.

* * * * *

SEQUENCE LISTING

<160> NUMBER OF SEQ ID NOS: 1

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35              40                  45

Val Met Ala Ser Phe Tyr Lys Ala Glu Glu Leu Tyr Gln
    50                  55                  60